United States Patent [19]

Björnson et al.

[11] 4,038,310

[45] July 26, 1977

[54] ACID ANHYDRIDE TO REACT WITH IMPURITIES IN THE PRODUCTION OF PERFLUOROCARBOXYLIC ACIDS

[75] Inventors: Geir Björnson; Harold C. Walters, both of Bartlesville, Okla.

[73] Assignee: Phillips Petroleum Company, Bartlesville, Okla.

[21] Appl. No.: 666,092

[22] Filed: Mar. 11, 1976

[51] Int. Cl.$^2$ .................... C07C 53/18; C07C 53/34
[52] U.S. Cl. .................... 260/539 A; 204/59 F; 260/408; 260/537 S; 260/539 R; 260/544 F
[58] Field of Search ............ 260/539 R, 539 A, 408, 260/537 S, 544 F

[56] References Cited

U.S. PATENT DOCUMENTS

| | | | |
|---|---|---|---|
| 3,213,062 | 10/1965 | Ellingboe et al. | 260/63 |
| 3,318,950 | 5/1967 | Christoph et al. | 260/544 |
| 3,576,860 | 4/1971 | Zazaris | 260/539 |

OTHER PUBLICATIONS

Simmons, Chemical Reviews, vol. 8, p. 213 (1931).

*Primary Examiner*—Jane S. Myers

[57] ABSTRACT

Perfluorocarboxylic acids are produced by a metathesis reaction between an acid and a perfluoro acid fluoride in the presence of an acid anhydride. The perfluoroacid fluoride can conveniently be produced by electrochemical fluorination of the acyl fluoride co-product of the metathesis step. The acid anhydride present during the metathesis reaction serves the dual function of enhancing the desired reaction to produce the perfluorocarboxylic acid product and to react with impurities and by-products which would otherwise remain with the product and complicate its recovery.

9 Claims, 1 Drawing Figure

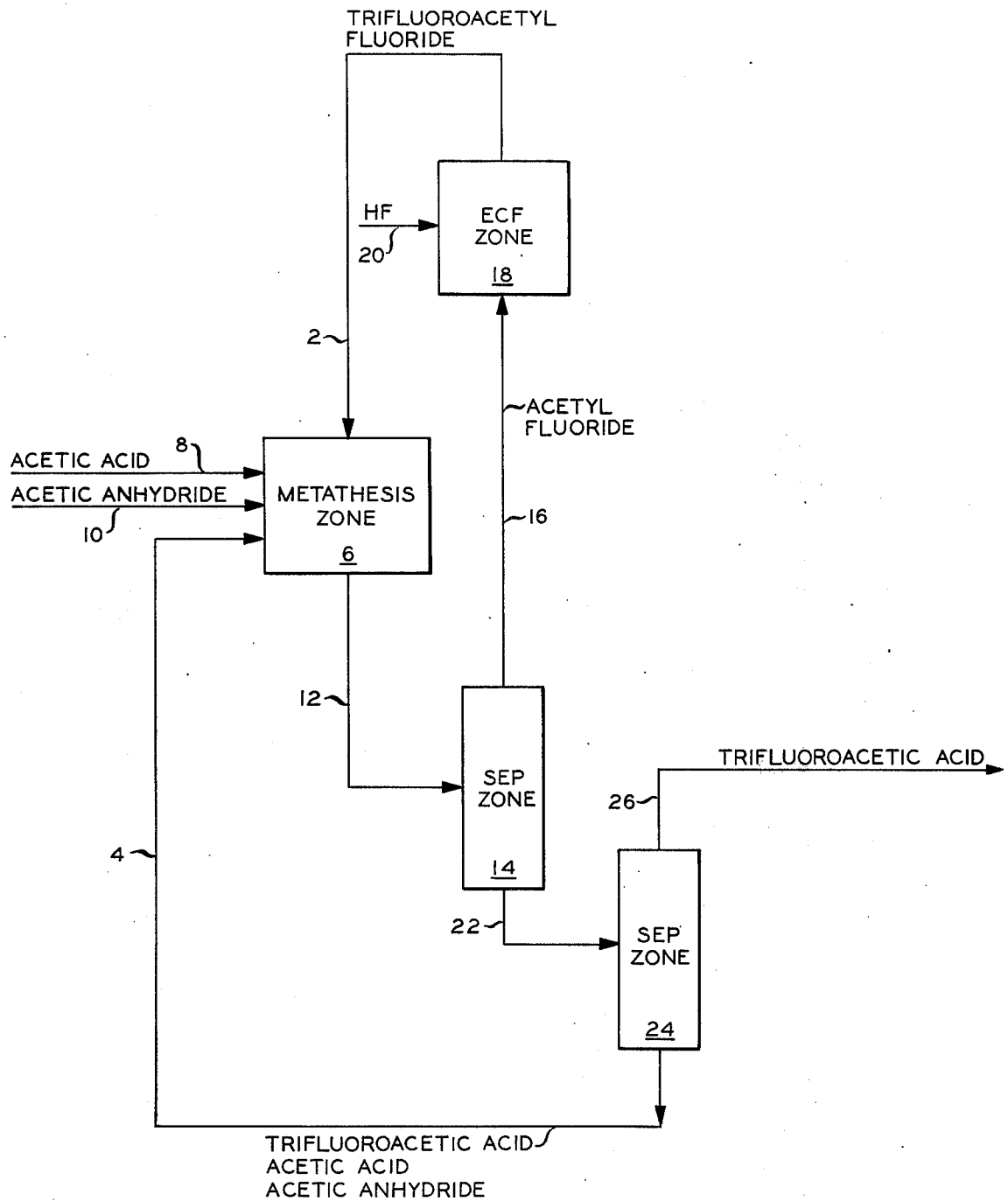

ACID ANHYDRIDE TO REACT WITH IMPURITIES IN THE PRODUCTION OF PERFLUOROCARBOXYLIC ACIDS

BACKGROUND OF THE INVENTION

This invention relates to the production of perfluorocarboxylic acids by means of a metathesis reaction between a perfluorocarboxylic acid fluoride and an alkanoic acid.

Perfluorocarboxylic acids are items of commerce which have a broad scope of utility. For example, perfluorooctanoic acid can be used as a reagent to provide fluorine-containing groups on a polymer molecule thus imparting water-repellency and soil-resistance to fibers and fabrics prepared from such a modified polymer. Similarly, trifluoroacetic acid can be used as a catalyst and is a chemical intermediate in the production of pharmaceutical, agricultural, and industrial products.

The production of perfluorocarboxylic acids utilizing electrochemical techniques is known and recent developments in the field of electrochemical fluorination chemistry have made such techniques even more attractive, However, the primary cell products of such electrochemical fluorination techniques are invariably in the form of the acid fluorides, e.g., trifluoroacetyl fluoride. Thus, in order to obtain the desired perfluorocarboxylic acid, e.g., trifluoracetic acid, this primary cell product must be converted to the free acid. This can be done by a metathesis reaction between the perfluoroacid fluoride and a carboxylic acid. The electrochemical process and the metathesis reaction, however, result in the formation of undesirable contaminants and by-products such as HF, $H_2O$ and/or carbonyl fluoride.

As mentioned above, electrochemical fluorination is a convenient process for producing the perfluoroacyl fluoride starting materials for the metathesis reaction. Though electrochemical fluorination is an efficient process, its perfluoroacyl fluoride cell product contains minor amounts of by-products such as carbonyl fluoride and hydrogen fluoride. Such materials are difficultly removable from the primary product because of similar boiling points, a tendency to form complexes, or other reasons. In addition, there are always opportunities for the introduction of small amounts of extraneous water into the system. The presence of minor amounts of materials such as hydrogen fluoride, carbonyl fluoride, or water has been found to hinder the above-described metathesis reaction and/or to complicate the isolation and/or recovery of the desired metathesis product.

SUMMARY OF THE INVENTION

It is an object of this invention to provide perfluorocarboxylic acids from free alkanoic acids;

It is a further object to provide perfluorocarboxylic acids by reacting alkanoic acids with perfluorocarboxylic acid fluorides which contain minor amounts of impurities such as carbonyl fluoride, hydrogen fluoride, or water;

It is yet a further object of this invention to provide unitized combination process which conveniently utilizes more available and more economical free carboxylic acids as basic raw materials for the production of perfluorocarboxylic acids; and It is still yet a further object of this invention to facilitate the separation of the desired perfluorocarboxylic acid product from the effluent of a metathesis reaction.

In accordance with this invention, an alkanoic acid is reacted with a perfluorocarboxylic acid fluoride to produce perfluorocarboxylic acid and alkanoic acid fluoride with a small amount of an alkanoic acid anhydride being utilized to react with impurities.

BRIEF DESCRIPTION OF THE DRAWING

The FIGURE, which forms a part hereof, shows in schematic form a simplified flow chart for the production of perfluorocarboxylic acid utilizing an acid anhydride in the metathesis reaction.

DESCRIPTION OF THE PREFERRED EMBODIMENTS

The metathesis reaction utilizing an anhydride to react with impurities can be carried out in any of the following four embodiments:

According to Embodiment I, perfluorocarboxylic acids are prepared by a procedure comprising:

1. contacting an alkanoic acid, under reaction conditions, with a perfluorocarboxylic acid fluoride to produce an alkanoic acid fluoride and a perfluorocarboxylic acid utilizing an acid anhydride to react with impurities.

This is the simplest form of the invention and involves simply carrying out the metathesis reaction between a perfluorocarboxylic acid fluoride, which contains impurities such as carbonyl fluoride, hydrogen fluoride, or water, and an unsubstituted carboxylic acid in the presence of a minor amount of a carboxylic acid anhydride. Preferably, the appropriate amount of carboxylic acid anhydride is introduced at the beginning of the metathesis reaction. However, at least some beneficial results can be obtained if it is introduced at any time up to the completion of the metathesis reaction.

According to Embodiment II of the present invention, a carboxylic acid is converted to a perfluorocarboxylic acid by a procedure comprising:

1. contacting a carboxylic acid, under reaction conditions, with a perfluorocarboxylic acid fluoride to produce a carboxylic acid fluoride and a perfluorocarboxylic acid product utilizing an acid anhydride to react with impurities;
2. subjecting the alkanoic acid fluoride from step (1) to electrochemical fluorination to produce a perfluorocarboxylic acid fluoride; and
3. passing the perfluorocarboxylic acid fluoride from step (2) to step (1).

According to Embodiment III of the present invention, a perfluorocarboxylic acid fluoride containing minor amounts of impurities such as carbonyl fluoride, hydrogen fluoride, or water, is converted to a perfluorocarboxylic acid by a procedure comprising:

1. contacting a carboxylic acid, under reaction conditions, with a perfluorocarboxylic acid fluoride in the presence of a minor amount of carboxylic acid anhydride to produce a reaction mixture containing a carboxylic acid fluoride and a perfluorocarboxylic acid;
2. subjecting the reaction mixture of step (1 ) to a separation operation to produce a perfluorocarboxylic acid product stream, a carboxylic acid fluoride by-product stream, and a residual stream comprising a mixture of perfluorocarboxylic acid, carboxylic acid, and carboxylic acid anhydride; and
3. passing the residual stream of step (2) to the reaction zone of step (1).

Thus, Embodiment III outlined above defines a process by which a perfluorocarboxylic acid fluoride, which contains typical impurities, can be efficiently converted to the corresponding perfluorocarboxylic acid. Moreover, this product can be efficiently recovered in high purity despite the initial presence of impurities, such as carbonyl fluoride, hydrogen fluoride, and water which tend to complicate convenient separation and which contribute to chemical losses, particularly losses of fluoride values.

According to Embodiment IV of the present invention, a carboxylic acid is converted to a perfluorocarboxylic acid by a procedure comprising:

1. contacting a carboxylic acid, under reaction conditions, with a perfluorocarboxylic acid fluoride, in the presence of a minor amount of carboxylic acid anhydride, to produce a reaction mixture containing a carboxylic acid fluoride and a perfluorocarboxylic acid;
2. subjecting the reaction mixture of step (1) to separation operation to produce a carboxylic acid fluoride stream and a perfluorocarboxylic acid fluoride-containing stream;
3. passing the carboxylic acid fluoride from step (2) to an electrochemical fluorination zone to produce perfluorocarboxylic acid fluoride;
4. passing the perfluorocarboxylic acid fluoride from step (3) to step (1);
5. subjecting the perfluorocarboxylic acid-containing stream from step (2) to a separation operation to produce a perfluorocarboxylic acid product stream, and a residual stream comprising a mixture of perfluorocarboxylic acid, carboxylic acid, and carboxylic acid anhydride; and
6. passing the residual stream of step (5) to the reaction zone of step (1).

Thus, Embodiment IV outlined above defines a convenient and efficient sequence of steps, including metathesis reactions, electrochemical fluorination reactions, and separations steps, by which carboxylic acids can be converted to perfluorocarboxylic acids. This process substantially overcomes chemical losses and separations difficulties that might otherwise be incurred due to the presence in the system of impurities which are typical of perfluorocarboxylic acid fluorides produced by electrochemical fluorination.

The impurities removed by the acid anhydride in accordance with this invention are primarily carbonyl fluoride and hydrogen fluoride. Lesser amounts of water and other impurities may also be removed. The carbonyl fluoride and hydrogen fluoride impurities originate with the perfluorocarboxylic acid fluoride feedstock, being formed during the electrochemical fluorination of a carboxylic acid fluoride to give the perfluorocarboxylic acid fluoride feedstock. The water is the result of some moisture unavoidably being present in the feedstock or otherwise getting into the reactor.

Generally, the carbonyl fluoride is present in an amount within the range of 0.1 to 10 weight percent and the hydrogen fluoride 0.1 to 10 weight percent based on the total weight of the perfluorocarboxylic acid fluoride feedstock. It is essential to provide sufficient acid anhydride to react with essentially all of these impurities since even trace amounts of hydrogen fluoride cause corrosion. A large excess of the anhydride is undesirable, however, since a large excess apparently results in the formation of perfluorocarboxylic acid anhydrides which are difficult to separate from the products.

Thus, the acid anhydride is preferably added in an amount within the range of 1 to 1.5, preferably 1.0 to 1.25, moles of anhydride for each mole of impurity. That is, if there were present 0.5 mole of carbonyl fluoride and 0.5 mole of hydrogen fluoride for a total of 1 mole, then 1 to 1.5 moles of anhydride would be used. While the reaction can be allowed to go nearly to completion and then the anhydride added (in which case it can be titrated in with the addition stopping just as soon as all of the impurities are reacted), it is preferred to add it along with the metathesis reactants.

While the amount of alkanoic acid anhydride added is related to the amount of impurities, it has been found that the typical level of impurities in the perfluorocarboxylic acid fluoride from an electrochemical fluorination are such that about 5 to 20, preferably 10 to 15, mole percent anhydride based on the moles of perfluorocarboxylic acid fluoride is satisfactory within the metathesis reaction zone. In the event that a particular feedstock has a different level of impurity, this can be easily calculated and the amount of anhydride adjusted accordingly.

Although it is not intended to limit the scope of the present invention, the following simplified chemical equations further describe and illustrate the basic chemical transformations involved in the present invention using specific exemplary feedstocks:

| Conversion of Perfluorocarboxylic Acid Fluoride to Perfluorocarboxylic Acid |
|---|
| Metathesis Step |

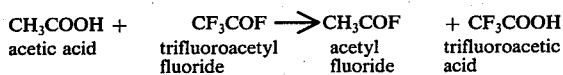

| $CH_3COOH$ + | $CF_3COF \longrightarrow CH_3COF$ | + $CF_3COOH$ |
|---|---|---|
| acetic acid | trifluoroacetyl     acetyl | trifluoroacetic |
| | fluoride           fluoride | acid |

The chemical equation above illustrates the efficient, convenient conversion of a perfluorocarboxylic acid fluoride into the corresponding perfluorocarboxylic acid. Other higher carboxylic acids can undergo this transformation with similar advantage.

| Production of Perfluorocarboxylic Acid From Carboxylic Acid |
|---|
| Metathesis Step |

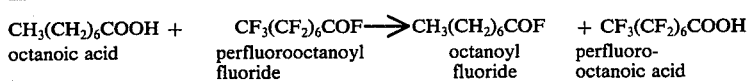

| $CH_3(CH_2)_6COOH$ + | $CF_3(CF_2)_6COF \longrightarrow CH_3(CH_2)_6COF$ | + $CF_3(CF_2)_6COOH$ |
|---|---|---|
| octanoic acid | perfluorooctanoyl     octanoyl | perfluoro- |
| | fluoride           fluoride | octanoic acid |

Electrochemical Fluorination Step

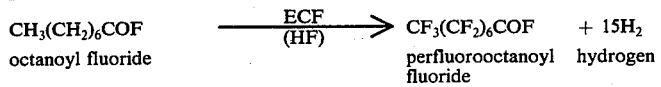

| $CH_3(CH_2)_6COF$ | $\xrightarrow{\text{ECF} \atop \text{(HF)}}$ | $CF_3(CF_2)_6COF$ | + $15H_2$ |
|---|---|---|---|
| octanoyl fluoride | | perfluorooctanoyl fluoride | hydrogen |

The equations above illustrate a combination of steps which cooperate in a particularly advantageous way. In the metathesis step, the octanoic acid feed is converted to octanoyl fluoride which is a highly desirable form of this feedstock for introduction to an electrochemical cell. That same metathesis step, advantageously, converts the corresponding perfluorooctanoyl fluoride to the desired perfluorooctanoic acid product.

In theory, sufficient perfluorooctanoyl fluoride is generated in the electrochemical fluorination step to sustain the metathesis step. In actual operation, however, some mechanical and/or chemical losses of intermediates or products can be incurred. Therefore, to keep the process operating on a truly continuous basis it may be necessary to provide make-up amounts of the acyl fluoride, such as octanoyl fluoride, in minor amounts to the ECF step. This minor amount of make-up acyl fluoride can be obtained from any suitable source.

The reaction of the anhydride with impurities is as follows, again acetic anhydride and the corresponding products being selected for the purpose of illustration only.

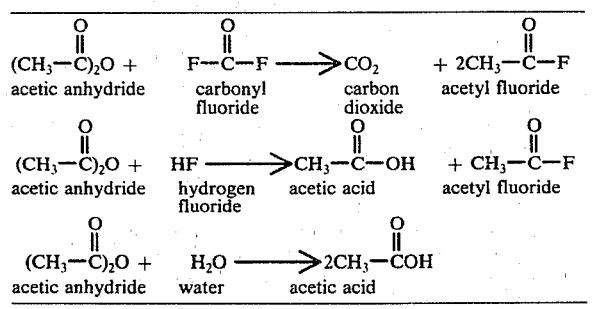

The feedstocks which are applicable for the metathesis step of the present invention are alkanoic acids such as mono- and dicarboxylic acids containing from 2 to about 10 carbon atoms per molecule. Some examples of these are acetic acid, propionic acid, butyric acid, 3-methylbutyric acid, succinic acid, valeric acid, adipic acid, caproic acid, octanoic acid, decanoic acid, and the like, and mixtures thereof. Monoalkanoic acids are presently preferred.

In Embodiment I wherein a carboxylic acid is reacted with a perfluorocarboxylic acid fluoride, the scope of the applicable fluorinated acid fluoride is the same as that of the nonfluorinated acids described above, that is containing from 2 to about 10 carbon atoms per molecule. In the other embodiments where the perfluoroacid fluoride for the metathesis step is generated by electrochemical fluorination of the acid fluoride product produced by the metathesis step, the acid and perfluoroacid fluoride will obviously have the same number of carbon atoms. Generally, in Embodiment I the reactants are chosen so as to have the same number of carbon atoms also.

Similarly, the anhydride can be the anhydride of the above-described monocarboxylic alkanoic acids and can have from 4 to 20 carbon atoms per molecule, i.e., acetic anhydride through cupric anhydride. Since one of the products from the reaction of the anhydride with the carbonyl fluoride can be recycled to the electrochemical fluorination cell and one of the products from the reaction of the anhydride with the hydrogen fluoride can also be recycled to the electrochemical fluorination cell and the other to the metathesis reaction, the anhydride preferably corresponds to the acid of the metathesis reaction.

The metathesis reaction is an efficient and convenient reaction. It is exothermic and can be substantially quantitative because, though an equilibrium reaction, high concentrations of the desired products are surprisingly favored. The molar proportions of carboxylic acid to perfluorinated carboxylic acid fluoride can vary depending upon convenience and the extent of conversion desired but will generally be in the range of from about 0.5:1 to 2:1. If quantitative or near quantitative conversion of the perfluorocarboxylic acid fluoride is desired, at least one mole, and preferably more, of alkanoic acid is present for each mole of the perfluorocarboxylic acid fluoride. Preferably, the molar ratio is in the range of 1:1 to about 1.3:1 moles of alkanoic acid to moles of perfluorocarboxylic acid fluoride.

The contact of the carboxylic acid and the perfluorocarboxylic acid fluoride in the presence of an acid anhydride can be carried out either batchwise or continuously under any suitable reaction conditions, including temperature, pressure and residence time, which will provide the desired degree of reaction. The temperature will generally be in the range of from about 0° to about 100° C., preferably from about 20° to about 50° C. Acetic acid, for example, melts at 16.6° C. and a temperature above the melting point of the components of the reaction mixture is preferred. The reaction can be carried out at any convenient pressure and the pressure will generally be in the range of from 0 to about 7,000 k Pa. The reaction time will generally be in the range from about 0.1 to about 100 minutes.

The conversion of the alkanoic carboxylic acid fluoride to the perfluorocarboxylic acid fluoride can be carried out using any suitable electrochemical fluorination procedure which is presently known in the art. Thus, electrochemical fluorination processes wherein the feedstock is dissolved in the liquid electrolyte, such as disclosed in U.S. Pat. No. 2,519,983, can be employed. Electrochemical processes wherein the feedstock is bubbled through a porous anode into the liquid electrolyte, such as disclosed in U.S. Pat. No. 3,298,940, can also be employed.

Particularly suitable are the electrochemical procedures disclosed in U.S. Pat. Nos. 3,511,760, 3,511,762, and 3,711,396, the contents of which are hereby incorporated into this disclosure by reference. The processes described in these patents feature a mode of reaction in which the fluorinatable feedstock, either in the presence or absence of a carrier gas, is passed into the pores of suitable porous anodes immersed in a suitable liquid electrolyte such that the feedstock and the resulting fluorinated products have no appreciable contact with the bulk of the liquid electrolyte outside the pores of the porous anode. Such a mode of operation has been found to offer significant advantages in efficiency and selectivity to desired products.

After leaving the fluorination cell, the perfluorocarboxylic acid fluoride cell products are separated, using conventional means, to remove incompletely fluorinated materials, hydrogen, and other by-products. As indicated above, the perfluorocarboxylic acid stream can still retain minor amounts of some impurities including carbonyl fluoride and hydrogen fluoride.

The FIGURE is a simplified flow diagram for the production of perfluorocarboxylic acids using an acid anhydride to react with impurities. As a nonlimiting example, the invention process in the FIGURE is described in terms of converting acetic acid into trifluoroacetic acid using acetic anhydride to react with impurities.

In the FIGURE, trifluoroacetyl fluoride via line 2, and a residual stream comprising a mixture of trifluoroacetic acid, acetic acid, and acetic anhydride via line 4 is passed into metathesis reaction zone 6. Also passed into reaction zone 6 are make-up amounts of acetic acid via line 8 and acetic anhydride via line 10.

Metathesis zone 6 can comprise one or more chemical reactors and associated apparatus such as heat exchangers, control means, pumps, valves and the like, which are sufficient to promote the reaction of trifluoroacetyl fluoride with acetic acid to produce acetyl fluoride and trifluoroacetic acid. The reaction can be carried out batchwise or continuously.

Effluent from metathesis zone 6 is passed via line 12 into separation zone 14. Separation zone 14 can comprise one or more separation means such as distillation apparatus, absorption units, adsorption units, and the like together with associated pumps, heaters, heat exchangers and the like which are sufficient to provide a separated stream consisting essentially of acetyl fluoride in line 16. Minor amounts of low boiling components such as carbon dioxide can also be removed (not shown) in this zone. The separations can be carried out batchwise or continuously.

A preferred mode of operation employs a relatively short residence time at a relatively low temperature to minimize the back reaction of acetyl fluoride with trifluoroacetic acid. In one convenient method, the effluent from metathesis zone 6 is continuously fed into the middle of a distillation column which is refluxing with a mixture comprising acetic acid and trifluoroacetic acid. Under such conditions, the acetyl fluoride is flashed overhead and out of contact with the acetic acid.

Acetyl fluoride is passed via line 16 into electrochemical fluorination (ECF) zone 18. Electrochemical fluorination zone 18 can comprise one or more electrolytic cells together with associated separation means for recovering product trifluoroacetyl fluoride and recycling incompletely fluorinated materials (not shown). Hydrogen fluoride is passed into the electrolytic zone through line 20 and hydrogen (not shown) leaves this zone as a by-product. The trifluoroacetyl fluoride leaves the electrolytic zone 18 and passes via line 2 into metathesis zone 6.

The heavier, trifluoroacetic acid-containing product from separation zone 14 is passed via line 22 into separation zone 24. Separation zone 24 can comprise one or more conventional separation means and associated apparatus similar to separation zone 14 which are sufficient to provide a separated stream consisting essentially of trifluoroacetic acid product in line 26. The separation can be carried out continuously or batchwise. Fractionation apparatus is particularly convenient.

If desired, separation zone 14 can be combined with separation zone 24 in a batchwise operation in which the metathesis effluent in line 12 is passed into the center of a fractionating column such that the acetyl fluoride is flashed overhead while the trifluoroacetic acid, acetic acid, and acetic anhydride are allowed to flow down the column into the kettle. When this operation is finished, the upper section of the column is allowed to reach the boiling point of the trifluoroacetic acid product and a batch distillation is carried out to recover this product.

The separation and recovery of trifluoroacetic acid can be conveniently carried out up to a point at which the remaining trifluoroacetic acid is about equimolar with the amount of acetic acid present. These two materials form a dimer which is broken by elevated temperature. However, it is convenient merely to recycle this residual material, such as the kettle bottoms of a distillation, back to the metathesis zone 6 via line 4. This residual material thus contains trifluoroacetic acid, and surviving amounts of acetic acid and acetic anhydride. The amounts of acetic acid and acetic anhydride which are recycled via line 4 to metathesis zone 6 will determine the amounts of make-up acetic acid and acetic anhydride passed into metathesis zone 6 via lines 8 and 10, respectively, to provide the desired ratios of reactants.

The carboxylic acid anhydrides, such as acetic anhydride, have been found to perform several functions which are advantageous for the process of the present invention. The perfluorocarboxylic acid fluorides, such as trifluoroacetyl fluoride, from the electrochemical fluorination cell contains carbonyl fluoride and hydrogen fluoride. The acid anhydride reacts with HF to yield recyclable products such as acetyl fluoride and acetic acid. Similarly, acetic anhydride converts carbonyl fluoride to carbon dioxide and acetyl fluoride. Thus, fluorine values in such by-product impurities are not lost but recovered in readily usable form. Also, the acid anhydrides keep the system dry by reacting with extraneous water to form acetic acid. Water is undesirable because it readily hydrolyzes acid fluorides and products HF. The presence of HF is undesirable because in admixture with acids such as acetic acid it is extremely corrosive and requires relatively costly materials of unsaturation to contain it.

Hydrogen fluoride also somewhat inhibits the metathesis reaction by forming a complex with carbonyl groups. It also complexes with trifluoroacetic acid and thus purification by distillation is more difficult. Finally, HF promotes condensation reactions which lead to tarry residues after distillation. This causes loss of product and a disposal problem.

EXAMPLE I

In this example, trifluoroacetyl fluoride was reacted with glacial acetic acid in a one-step reaction to produce trifluoroacetic acid and acetyl fluoride. The trifluoroacetyl fluoride feedstock, produced by electrochemical fluorination of acetyl fluoride, contained about 2 weight percent carbonyl fluoride by-product and about 0.6 weight percent hydrogen fluoride.

A gaseous stream of this feedstock was slowly bubbled into 28.82 g (0.48 mole) of glacial acetic acid contained in a 76 cc glass reaction tube immersed in a water bath. In addition to the acetic acid, the reaction tube also contained 3.05 g (0.030 mole) acetic anhydride to destroy the carbonyl fluoride and hydrogen fluoride contaminants in the feedstock.

A total of 49.7 g (0.43 mole) of the trifluoroacetyl fluoride feedstock was passed into the reaction tube over a period of about 1.5 hours. During this period the reaction pressure varied from about 0 to about 180 psig and the reaction temperature increased from about 19° C. to about 43° C. The reaction mixture was then allowed to stand about 2 hours at room temperature.

Distillation of the reaction mixture yielded trifluoroacetic acid, acetyl fluoride, and acetic acid. A middle cut was taken and was confirmed by nuclear magnetic resonance (NMR) spectroscopy to be trifluoroacetic acid. This cut was analyzed by GLC and found to be greater than 99 weight percent pure, containing only minor amounts of acetic acid and acetyl fluoride. The material balance of the reaction was also consistent with the essentially quantitative reaction:

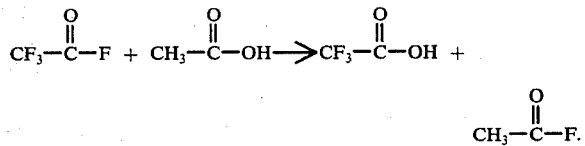

Thus, the preceding example demonstrated the one-step reaction of Embodiment I of the present invention in that it showed the conversion of a perfluorocarboxylic acid fluoride to a perfluorocarboxylic acid using acetic anhydride to react with impurities.

EXAMPLE II

The following run illustrates the metathetical reaction of impure heptafluorobutyryl fluoride with butyric acid in the presence of butyric anhydride to give heptafluorobutyric acid and butyryl fluoride and the recovery of products from the reaction mixture by fractional distillation.

The impure heptafluorobutyryl fluoride employed in this run was the effluent from an electrochemical fluorination cell in which butyryl fluoride was converted to heptafluorobutyryl fluoride. The effluent was 96 or more weight percent heptafluorobutyryl fluoride, 4 or less weight percent hydrogen fluoride and a trace of carbonyl fluoride.

Into a 10 gallon (38 l) stainless steel stirred autoclave reactor were placed 22.7 lbs. (0.258 lb.-moles, 10.3 kg) butyric acid and 14.7 lbs. (0.093 lb.-moles, 6.6 kg) butyric anhydride. After the reactor was sealed 46.8 lbs. (21 kg) of the above-described effluent containing heptafluorobutyryl fluoride (at least 0.206 lb.-mole) and hydrogen fluoride (0.093 lb.-mole or less) was added with constant stirring to the reactor at 26° C. over a period of 17 minutes during which time the reaction temperature and pressure increased to 40° C. and 66 psig (455 k Pa), respectively. The reaction mixture was stirred continuously for 1 hour after which 10.25 lbs. (0.046 lb.-mole, 4.6 kg) additional impure heptafluorobutyryl fluoride was added over a 3-minute period. The reaction mixture was distilled through a 1.7 m column packed with 6.5 mm carbon Raschig rings to give 29.75 lbs. (13.5 kg, 55.2 percent of theoretical yield) of heptafluorobutyric acid (b.p. 116–119° C. at 100 k Pa) and 25.75 lbs. (11.6 kg, 113.5 percent of theoretical yield based on heptafluorobutyryl fluoride reactant or 83 percent of theoretical yield based on heptafluorobutyryl fluoride and hydrogen fluoride reactants) of butyryl fluoride (b.p. 58° C. at 100 k Pa). The distillation and recovery of fractions was observed to proceed smoothly. The product fractions were stored in glass containers without evidence of hydrogen fluoride-etching of the glass.

EXAMPLE III

The following comparative run illustrates the metathetical reaction of impure heptafluorobutyryl fluoride with butyric acid described in Example II but with an insufficient amount of butyric anhydride to react with the hydrogen fluoride present as impurity and the recovery of products by fractional distillation.

The impure heptafluorobutyryl fluoride employed in this comparative run was the effluent from an electrochemical fluorination cell in which butyryl fluoride was converted to heptafluorobutyryl fluoride. The effluent was 89 percent heptafluorobutyryl fluoride and 8.4 weight percent hydrogen fluoride with the balance being carbonyl fluoride and other fluorine-containing compounds.

Into a 10 gallon (38 l) stainless steel stirred autoclave reactor were placed 15.2 lbs. (6.9 kg, 0.173 lb.-mole) butyric acid and 11.7 lbs. (5.3 kg, 0.074 lb.-mole) butyric anhydride. After the reactor was sealed, 55.0 lbs. (25 kg) of the above-described effluent containing heptafluorobutyryl fluoride (0.223 lb.-mole) and hydrogen fluoride (0.231 lb.-mole) was added with constant stirring to the reactor at 24° C. over a period of 70 minutes during which time the reaction temperature and pressure increased to 35° C. and 100 psig (690 k Pa), respectively.

A second run was made like the first except that the impure heptafluorobutyryl fluoride was added over a 40 minute period with increases of reaction temperature and pressure to 40° C. and 55 psig (379 k Pa), respectively. The two reaction mixtures were combined and subjected to fractional distillation through a 1.7 m column packed with 6.5 mm carbon Raschig rings. A fraction containing predominantly butyryl fluoride and distilling at 48° C. at 100 k Pa (compared to 58° C. in Example II) reacted vigorously with a soft glass storage bottle indicating the presence of hydrogen fluoride. Likewise, the fraction containing predominantly heptafluorobutyric acid reacted vigorously with a soft glass storage bottle indicating the presence of hydrogen fluoride.

The yield of heptafluorobutyric acid was only about 50 percent because the HF caused part of the kettle contents to condense to a tar.

Thus, the inventive run yielded butyryl fluoride and heptafluorobutyric acid free from detectable amounts of hydrogen fluoride, while the comparative run which was made with insufficient butyric anhydride to react with the hydrogen fluoride and carbonyl fluoride present as impurities in the feedstock yielded butyryl fluoride and less heptafluorobutyric acid both containing sufficient hydrogen fluoride to prevent storage in glass containers.

While this invention has been described in detail for the purpose of illustration, it is not to be construed as limited thereby but is intended to cover all changes and modifications within the spirit and scope thereof.

We claim:

1. In a process comprising contacting under reaction conditions an alkanoic carboxylic acid containing 2 to 10 carbon atoms per molecule, and a perfluorocarboxylic acid fluoride containing 2 to 10 carbon atoms per molecule from an electrochemical fluorination zone to give a perfluorocarboxylic acid and an acyl fluoride, the improvement comprising adding a small amount of an alkanoic acid anhydride to react with impurities, said impurities including at least one of HF, water, and carbonyl fluoride.

2. A method in accordance with claim 1 wherein said contacting is carried out using a molar portion of alkanoic acid to perfluorocarboxylic acid fluoride in the range of 0.5:1 to 2:1 in a liquid state at a temperature within the range of 0°–100° C., a pressure within the range of 0–7,000 k Pa, the contact time being in the range of 0.1–100 minutes.

3. A method in accordance with claim 1 wherein said perfluorocarboxylic acid fluoride has the same number of carbon atoms as said alkanoic acid and said anhydride is the anhydride of said alkanoic acid.

4. A method in accordance with claim 1 wherein said alkanoic acid is acetic acid, said perfluorocarboxylic acid fluoride is trifluoroacetyl fluoride, said anhydride is acetic anhydride, said perfluorocarboxylic acid is trifluoroacetic acid and said acyl fluoride is acetyl fluoride.

5. A method according to claim 4 wherein said anhydride is added at the beginning of said contacting in an amount within the range of 10 to 15 mole percent based on the moles of said perfluorocarboxylic acid fluoride.

6. A method according to claim 4 wherein said anhydride is added at the beginning of said contacting in an amount within the range of 1.0 to 1.25 moles per mole of said impurities.

7. A method according to claim 1 wherein said acyl fluoride is passed to said electrochemical fluorination zone.

8. A method according to claim 1 wherein said anhydride is added in an amount within the range of 5 to 20 mole percent based on the moles of said perfluorocarboxylic acid fluoride.

9. A method according to claim 1 wherein said anhydride is added in an amount within the range of 1 to 1.5 moles of said anhydride per mole of said impurities.

* * * * *